US006489485B2

(12) United States Patent
Bizzarro et al.

(10) Patent No.: US 6,489,485 B2
(45) Date of Patent: Dec. 3, 2002

(54) PARA-AMINE SUBSTITUTED PHENYLAMIDE GLUCOKINASE ACTIVATORS

(75) Inventors: Fred Thomas Bizzarro, Colonia, NJ (US); Nancy-Ellen Haynes, Cranford, NJ (US); Ramakanth Sarabu, Cedar Grove, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/846,820

(22) Filed: May 1, 2001

(65) Prior Publication Data

US 2001/0051731 A1 Dec. 13, 2001

Related U.S. Application Data

(60) Provisional application No. 60/202,389, filed on May 8, 2000.
(51) Int. Cl.$^7$ ............................................. C07D 277/04
(52) U.S. Cl. ....................................................... 548/195
(58) Field of Search ......................................... 548/195

(56) References Cited

PUBLICATIONS

Chemical Abstracts 60:885d, "Effect of organic acids of pyridyl and thiazolylamides on certain memers of coli–typhosal, staphylococcal, streptococcal–groups and on acid–resistant myobacteria", vol. 60.*

Colowick, S.P., *The Enzymes*, vol. IX,Part B, pp. 1–48 (1973), Academic Press, NY.

Chipkin et al., *Joslin's Diabetes Mellitus, 13$^{th}$ Edition*, pp. 97–1165 (1994).

Olson, R. E. et al., *Annual Review of Nutrition*, vol. 13, pp 463–496 (1993).

Meglasson, M..D., et al.,*Amer. J. Physiol.* vol. 246, E1–E13 (1984).

Grupe, A. et al., *Cell*, vol. 83, pp. 69–78 (Oct. 1995).

Ferie, T. et al., *The FASEB Journal*, vol. 10, pp. 1213–1218 (1996).

Liang, Y., *Biochem. Journal*, vol. 305, pp. 167–173 (1995).

Glaser, B. et al. *New England Journal of Medicine*, vol. 338, pp. 226–230 (1998).

\* cited by examiner

*Primary Examiner*—Alan L. Rotman
*Assistant Examiner*—Binta Robinson
(74) *Attorney, Agent, or Firm*—George W. Johnston; Patricia S. Rocha-Tramaloni; Arthur D. Dawson

(57) ABSTRACT

Para-alkyl, aryl, cycloheteroalkyl or heteroaryl [carbonyl or sulfonyl] amino substituted phenyl amides active as glucokinase activators to increase insulin secretion which makes them useful for treating type II diabetes.

3 Claims, No Drawings

PARA-AMINE SUBSTITUTED PHENYLAMIDE GLUCOKINASE ACTIVATORS

PRIORITY TO PROVISIONAL APPLICATION(S) UNDER 35 U.S.C. §119(e)

This application claims priority under 35 U.S.C. §119(e) of provisional application Serial No. 60/202,389, filed on May 8, 2000.

BACKGROUND OF THE INVENTION

Glucokinase (GK) is one of four hexokinases found in mammals [Colowick, S. P., in *The Enzymes*, Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1–E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69–78, 1995; Ferrie, T., Riu, E., Bosch, F. et al., *FASEB J.*, 10, 1213–1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167–173, 1995). Additional evidence supporting an important role for GK in be the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226–230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

This invention provides an amide selected from the group consisting of a compound of the formula:

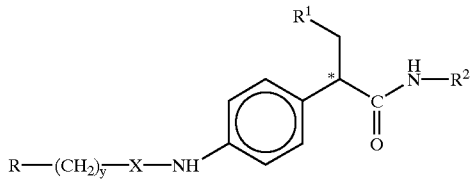

I wherein X is

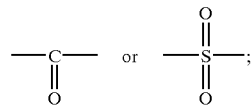

R is perfluoro-lower alkyl, lower alkyl,

lower alkoxycarbonyl, a heteroaromatic ring, connected by a ring carbon atom, containing from 5 to 6 ring members with from 1 to 3 heteroatoms selected from the group consisting of oxygen, sulfur and nitrogen, unsubstituted aryl containing 6 or 10 ring carbon atoms, a nitro or a lower alkyl substituted aryl, which aryl contains 6 or 10 ring carbon atoms, a saturated 5- to 6-membered cycloheteroalkyl ring, connected by a ring carbon atom, containing 1 or 2 heteroatoms selected from the group consisting of oxygen, sulfur and nitrogen, or a cycloalkyl ring having 5 or 6 carbon atoms; $R^1$ is a cycloalkyl having 5 or 6 carbon atoms; $R^2$ is a five- or six-membered heteroaromatic ring connected by a ring carbon atom to the amide group in the remainder of the compound, which heteroaromatic ring contains from 1 to 3 heteroatoms selected from the group consisting of oxygen, sulfur and nitrogen with a first heteroatom being nitrogen adjacent to the connecting ring carbon atom, said heteroaromatic ring being unsubstituted or monosubstituted at a position on a ring carbon atom other than adjacent to said connecting carbon atom with a substituent selected from the group consisting of lower alkyl, or

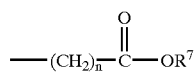

n and y independently are an integer of from 1 to 4, $R^4$, $R^5$ and $R^7$ are independently hydrogen or lower alkyl, and * denotes the asymmetric carbon atom and a pharmaceutically acceptable salt thereof.

The compounds of formula I are glucokinase activators useful for increasing insulin secretion in the treatment of type II diabetes.

DETAILED DESCRIPTION OF THE INVENTION

The compounds of formula I have the following embodiments

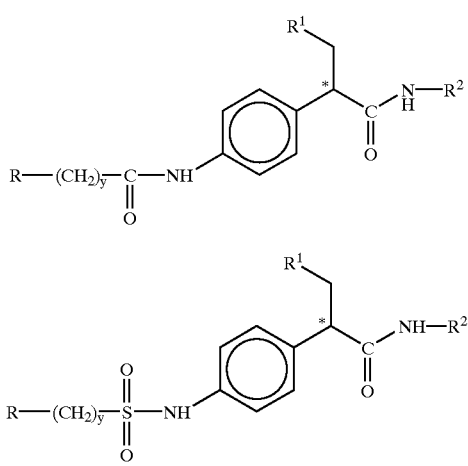

wherein R, $R^1$, $R^2$, * and y are as above;

In the compound of formulae I, IA and IB, the "*" designates that the asymmetric carbon atom in the compounds with the R optical configuration being preferred. The compounds of formula I may be present in the R or as a racemic or other mixtures of compounds having the R and S optical configuration at the asymmetric carbon shown. The pure R enantiomers are preferred.

As used throughout this application, the term "lower alkyl" includes both straight chain and branched chain alkyl groups having from 1 to 7 carbon atoms, such as methyl, ethyl, propyl, isopropyl, preferably methyl and ethyl. As used herein, the term "halogen or halo" unless otherwise stated, designates all four halogens, i.e. fluorine, chlorine, bromine and iodine.

As used herein, perfluoro-lower alkyl means any lower alkyl group wherein all of the hydrogens of the lower alkyl group are substituted or replaced by fluoro. Among the preferred perfluoro-lower alkyl groups are trifluoromethyl, pentafluoroethyl, heptafluoropropyl, etc.

As used herein, the term "aryl" signifies "polynuclear" and mononuclear unsubstituted aromatic hydrocarbon groups such as phenyl, naphthy containing either 6 or 10 carbon atoms which aryl groups in the compounds of formulae I, IA and IB are either phenyl and naphthyl. The aryl substituent can be unsubstituted or substituted, preferably monosubstituted with a nitro or lower alkyl substituted.

R can be any five- or six-membered saturated cycloheteroalkyl ring containing from 1 to 2 heteroatoms selected from the group consisting of sulfur, oxygen or nitrogen. Any such five- or six-membered saturated heterocyclic ring can be used in accordance with this invention. Among the preferred rings are morpholinyl, pyrrolidinyl, piperazinyl, piperidinyl, etc. When R is a saturated cyclic heteroacetyl ring, it is connected to the remainder of the molecule of formula I through a ring carbon atom.

The heteroaromatic ring defined by R and $R^2$ can be five- or six-membered heteroaromatic ring having from 1 to 3 heteroatoms selected from the group consisting of oxygen, nitrogen, and sulfur which is connected by a ring carbon to the remainder of the molecule as shown. The heteroaromatic ring defined by $R^2$ contains a first nitrogen heteroatom adjacent to the connecting ring carbon atom and if present, the other heteroatoms can be oxygen, sulfur, or nitrogen. Among the preferred heteroaromatic rings include pyridinyl, pyrimidinyl and thiazolyl. These heteroaromatic rings which constitute R are connected via a ring carbon atom to the amide group to form the amides of formula I. The ring carbon atom of the heteroaromatic ring which is connected to the amide to form the compound of formula I does not contain any substituent. When $R^2$ is an unsubstituted or mono-substituted five- or six-membered heteroaromatic ring, the rings contain a nitrogen heteroatom adjacent to the connecting ring carbon.

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

During the course of the reaction the various functional groups such as the free carboxylic acid will be protected via conventional hydrolyzable ester protecting groups. As used herein, the term "hydrolyzable ester" designates any ester conventionally used for protecting carboxylic acids which can be hydrolyzed to yield the respective carboxyl group. Exemplary ester groups useful for those purposes are those in which the acyl moieties are derived from a lower alkanoic, aryl lower alkanoic, or lower alkane dicarboxylic acid. Among the activated acids which can be utilized to form such groups are acid anhydrides, acid halides, preferably acid chlorides or acid bromides derived from aryl or lower alkanoic acids. Example of anhydrides are anhydrides derived from monocarboxylic acid such as acetic anhydride, benzoic acid anhydride, and lower alkane dicarboxylic acid anhydrides, e.g. succinic anhydride as well as chloro formates e.g. trichloro, ethylchloro formate being preferred.

Among the embodiments of the amides of formula I-A are those compounds where $R^1$ is cyclopentyl compounds of formula I-A1. The embodiments of the compounds of formula I-A1 are those compounds where $R^2$ is a 5-membered heteroaromatic ring, preferably thiazolyl. Among the embodiment of compounds of formula I-A1 are those compounds where $R^2$ is a 5-membered heteroaromatic ring are those compounds where R is:

aryl, preferably phenyl;

aryl substituted with a nitro group, preferably nitro substituted phenyl;

heteroaromatic ring such as pyrimidinyl, thiazolyl and pyridinyl; or lower alkoxy carbonyl.

Among other embodiments of the compounds of formula I-A1 are those compounds where $R^2$ is a substituted or unsubstituted 6-membered heteroaromatic ring such as pyridinyl. Among the embodiments of compounds of formula I-A1 where $R^2$ is a substituted or unsubstituted 6-membered heteroaromatic ring are those compounds where:

R is an unsubstituted aryl or a heteroaromatic ring, particularly pyridinyl;

R is lower alkoxy carbonyl; or

R is perfluoro-lower alkyl.

Among the embodiments of the compounds of formula I-B are those compounds wherein $R^1$ is cyclopentyl [compounds of formula I-B1]. Among the embodiments of compounds of formula I-B1 are those compounds where $R^2$ is a 5-membered heteroaromatic ring, preferably unsubstituted or substituted thiazolyl, with preferred embodiments being those compounds where R is a nitro substituted aryl such as nitro substituted phenyl;

aryl such as phenyl;

lower alkyl;

perfluoro-lower alkyl; or e)

where $R^4$ and $R^5$ are as above.

The compounds of formula I which are the compounds of formulae I-A and I-B are both prepared from the compound of the formula:

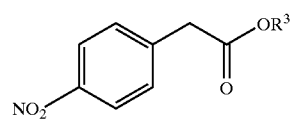

where $R^3$ taken together with its attached oxygen atom forms a hydrolyzable ester protecting group.

In accordance with an embodiment of this invention, the compound of formula II is converted to the compound of formula I-A via the following reaction scheme:

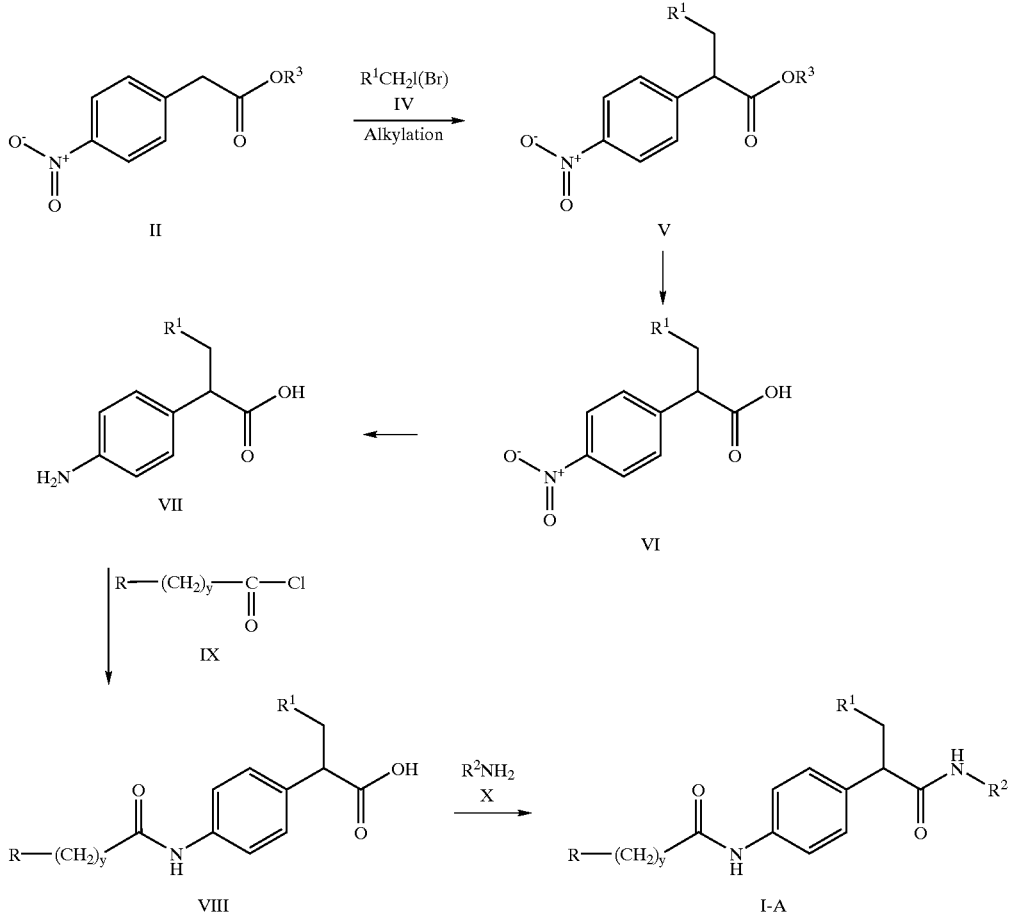

wherein R, $R^1$, $R^2$ and y are as above and $R^3$ taken together with its attached oxygen atom forms a hydrolyzable ester protecting group.

In the first step of this reaction, the compound of formula II is alkylated with the compound of formula IV to form the compound of formula V. Any conventional method of alkylating the alpha carbon atom of an organic acid ester with an alkyl bromide or iodide can be utilized to effect this conversion to produce the compound of formula V. In the next step of this reaction, the compound of formula V is hydrolyzed so as to remove the ester protecting group $R^3$. Any conventional method of ester hydrolysis can be utilized. Among the preferred methods is by treating the compound of formula V with lithium hydroxide in a mixed solvent of water and tetrahydrofuran. On the other hand, sodium hydroxide in methanol or other lower alkanols can be utilized to effect this hydrolysis. The compound of formula VI is converted to the compound of formula VII by reducing the nitro group to an amine group. Any conventional method of reducing a nitro to an amine group can be utilized in carrying out this reaction. Preferably, this reduction can be carried out by treating the compound of formula VI with hydrogen in the presence of a palladium on a carbon catalyst. Any of the conventional conditions for hydrogenation can be utilized in effecting this reduction. Hydrogenation in the presence of a palladium on carbon catalyst will not effect the carboxylic acid group on the compound of formula VI. The compound of formula VII is then converted to the compound of formula VIII by reacting the compound of formula VII with the compound of formula IX to acylate the free amino group. The compound of formula IX is an acid chloride and any conventional method of reacting an acid chloride with a primary amine can be utilized to effect this reaction. The compound of formula VIII is converted to the compound of formula I-A via reaction with the primary amine of formula X. Any conventional method of coupling a carboxylic acid such as the compound of formula VIII with a primary amine such as the compound of formula X produce an amide, i.e., the compound of formula I-A can be utilized to affect this coupling reaction.

The compound of formula I-B can be produced from the compound of formula VI above via the following reaction scheme:

amino group of the compound of formula XII with the sulfonyl chloride of formula XV to produce the sulfonamides of formula I-B. In carrying out this coupling reaction of a sulfonyl chloride with an amine, any conventional method for forming sulfonamides from sulfonyl chlorides and amines can be utilized. In this manner, the compound of formula I-B is produced.

If it is desired to produce the R enantiomer of the compound of formula I free of the other enantiomer, the compound of formula VI can be separated into this isomer from its racemate by any conventional chemical means. Among the preferred chemical means is to react the compound of formula VI with an optically active base. Any conventional optically active base can be utilized to carry out this resolution. Among the preferred optically active bases are the optically active amine bases such as alpha-methylbenzylamine, quinine, dehydroabietylamine and alpha-methylnaphthylamine. Any of the conventional techniques utilized in resolving organic acids with optically active organic amine bases can be utilized in carrying out this reaction.

In the resolution step, the compound of formula VI is reacted with the optically active base in an inert organic solvent medium to produce salts of the optically active

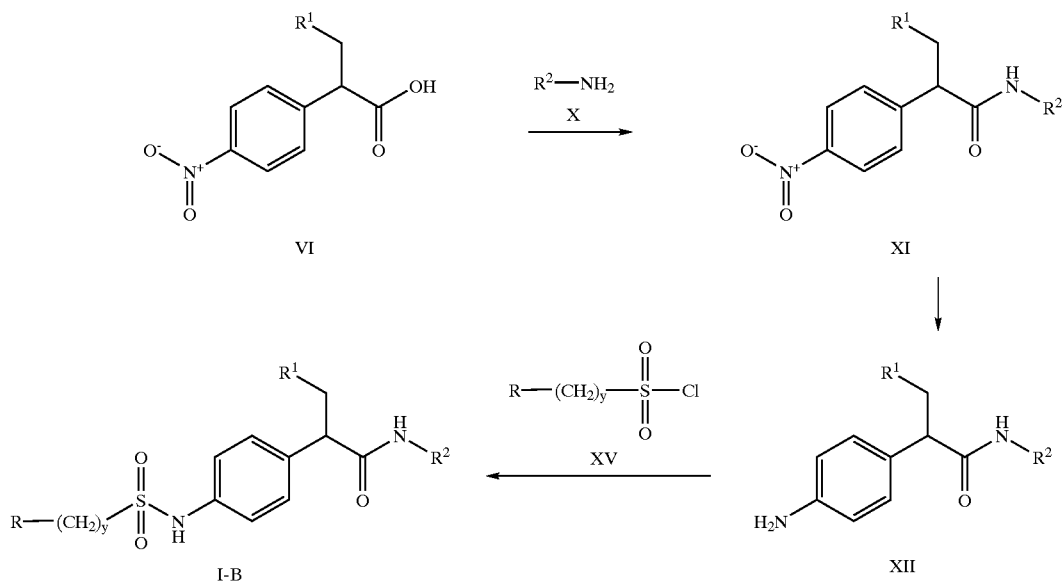

wherein R, $R^1$, $R^2$ and y are as above.

With respect to producing the sulfonamides, the compound of formula VI, as prepared by the aforementioned method, is utilized as a starting material. In this procedure, the compound of formula VI is reacted with the compound of formula X to produce the compound of formula XI. This reaction is carried out in the same manner as set forth with respect to the conversion of the compound of formula VIII to the compound of the formula I-A utilizing any conventional means of amide coupling. In the next step, the compound of formula XI is reduced via a hydrogenation in the presence of a hydrogenation catalyst such as palladium on carbon. This reaction is carried out in the same manner as previously described in connection with the hydrogenation of the compound of formula VI to the compound of formula VII. The compound of formula XII is then reacted with the compound of formula XV to produce the compound of formula I-B. This reaction is carried out by coupling the amine with both the R and S isomers of the compound of formula VI. In the formation of these salts, temperatures and pressure are not critical and the salt formation can take place at room temperature and atmospheric pressure. The R and S salts can be separated by any conventional method such as fractional crystallization. By means of measuring the optical rotation of the crystallized acid of formula VI, one can obtain the configuration of this crystalline material. If this crystallized acid has a negative rotation, then this crystallized acid has the R configuration. After crystallization, each of the salts can be converted to the respective compounds of formula VI in the R and S configuration by hydrolysis with an acid. Among the preferred acids are dilute aqueous acids, i.e., from about 0.001N to 2N aqueous acids, such as aqueous sulfuric or aqueous hydrochloric acid. The configuration of formula VI which is produced by this method of resolution is carried out throughout the entire reaction scheme to produce the desired R of formula I. The separation of R and S isomers can also be achieved using an enzymatic ester hydrolysis of any lower alkyl esters corresponding to the compound of the formula VI (see, for example, Ahmar, M.; Girard, C.; Bloch, R., *Tetrahedron Lett*, 1989, 7053), which results in the formation of corresponding chiral acid and chiral ester. The ester and the acid can be separated by any conventional method of separating an acid from an ester. The preferred method of resolution of racemates of the compounds of the formula VI is via the formation of corresponding diastereomeric esters or amides. These diastereomeric esters or amides can be prepared by coupling the carboxylic acids of the formula VI with a chiral alcohol, or a chiral amine. This reaction can be carried out using any conventional method of coupling a carboxylic acid with an alcohol or an amine. The corresponding diastereomers of compounds of the formula VI can then be separated using any conventional separation methods. The resulting pure diastereomeric esters or amides can then be hydrolyzed to yield the corresponding pure R and S isomers. The hydrolysis reaction can be carried out using any conventional method to hydrolyze an ester or an amide without racemization.

All of the compounds described in the Examples activated glucokinase in vitro in accordance with the assay described in Example A.

This invention will be better understood from the following examples, which are for purposes of illustration and are not intended to limit the invention defined in the claims that follow thereafter.

EXAMPLE 1

{N-{4-[2-Cyclopentyl-1-(thiazol-2-ylcarbamoyl)-ethyl]-phenyl}-benzamide

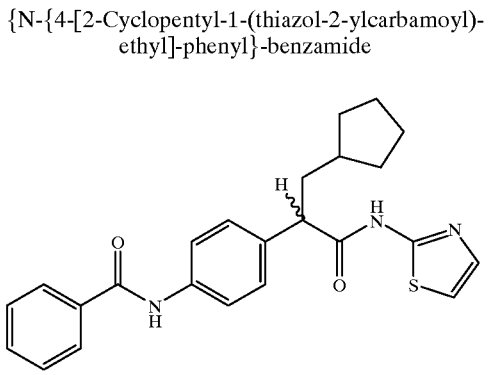

A solution of freshly prepared lithium diisopropylamide (430.55 mL of a 0.3M stock solution, 129.16 mmol) was cooled to −78° C. and then treated with a solution of (4-nitro-phenyl)-acetic acid ethyl ester (26.32 g, 125.83 mmol) in tetrahydrofuran/hexamethylphosphoramide (312.5 mL, 3:1). The resulting solution was stirred at −78° C. for 45 min. At this time, the reaction was treated with a solution of iodomethylcyclopentane (27.75 g, 132.1 mmol) in hexamethylphosphoramide (27.75 mL). The mixture was stirred at −78° C. for 4 h. The reaction was then warmed to 25° C. and was stirred at 25° C. for 16 h. At this time, the reaction mixture was quenched by the dropwise addition of a saturated aqueous ammonium chloride solution (250 mL). This mixture was concentrated in vacuo, diluted with water (250 mL), and extracted with ethyl acetate (3×300 mL). The combined organic extracts were washed with a saturated aqueous lithium chloride solution (2×250 mL), dried over magnesium sulfate, filtered, and concentrated in vacuo. Flash chromatography (Merck Silica gel 60, 230–400 mesh, 98/2 hexanes/ethyl acetate) afforded 3-cyclopentyl-2-(4-nitro-phenyl)-propionic acid ethyl ester (28.30 g, 77.2%) as a yellow oil: EI-HRMS m/e calcd for $C_{16}H_{21}NO_4$ (M$^+$) 291.1470, found 291.1470.

A solution of 3-cyclopentyl-2-(4-nitro-phenyl)-propionic acid ethyl ester (14.1 g, 48.06 mmol) in tetrahydrofuran/water (300 mL, 3:1) was treated with lithium hydroxide (4.35 g, 103.67 mmol). The reaction was stirred at 25° C. for 21 h. The tetrahydrofuran was then removed in vacuo. The residue was diluted with water (75 mL) and extracted with diethyl ether (3×75 mL). The aqueous layer was acidified to pH=1 with a 3N aqueous hydrochloric acid solution and then extracted with methylene chloride (3×75 mL). The combined organic extracts were washed with a saturated aqueous sodium chloride solution (2×100 mL), dried over magnesium sulfate, filtered, and concentrated in vacuo to give 3-cyclopentyl-2-(4-nitro-phenyl)-propionic acid (11.97 g, 93.6%) as a yellow solid: mp 119–125° C.; EI-HRMS m/e calcd for $C_{14}H_{17}NO_4$ (M$^+$) 263.1157, found 263.1162.

A solution of 3-cyclopentyl-2-(4-nitro-phenyl)-propionic acid (100 mg, 0.38 mmol) in ethyl acetate (50 mL) was treated with 10% palladium on activated carbon. The reaction mixture was stirred under 60 psi of hydrogen gas at 25° C. for 16 h. The catalyst was then removed by filtration through a pad of celite and washed with ethyl acetate. The filtrate was concentrated in vacuo to afford 2-(4-amino-phenyl)-3-cyclopentyl-propionic acid (120 mg, 100%) as a white solid: mp 167–169° C.; EI-HRMS m/e calcd for $C_{14}H_{19}NO_2$ (M$^+$) 233.1415, found 233.1413.

A solution of 2-(4-amino-phenyl)-3-cyclopentyl-propionic acid (49 mg, 0.21 mmol) in tetrahydrofuran (5 mL) was treated with N,N-diisopropylethylamine (0.04 mL, 0.25 mmol) and benzoyl chloride (0.02 mL, 0.21 mmol). The reaction mixture was stirred at 25° C. for 24 h. The reaction mixture was then concentrated in vacuo. Flash chromatography (Merck Silica gel 60, 230–400 mesh, 60/40 hexanes/ethyl acetate) afforded 2-(4-benzoylamino-phenyl)-3-cyclopentyl-propionic acid (41 mg, 57.9%) as a white solid: mp 192.5–194° C.; EI-HRMS m/e calcd for $C_{21}H_{23}NO_3$ (M$^+$) 337.1677, found 337.1670.

A solution of 2-(4-benzoylamino-phenyl)-3-cyclopentyl-propionic acid (20.2 mg, 0.06 mmol), benzotriazol-1-yloxytris(dimethylamino)phosphonium hexafluorophosphate (39.8 mg, 0.09 mmol), and 2-aminothiazole (9.0 mg, 0.09 mmol) in methylene chloride (2 mL) at 25° C. was treated with N,N-diisopropylethylamine (0.25 mL, 0.18 mmol). The reaction mixture was stirred at 25° C. for 16 h. At this time, the mixture was poured into water (50 mL) and extracted with ethyl acetate (3×25 mL). The combined organic extracts were washed with a 1N aqueous hydrochloric acid solution (1×25 mL), dried over sodium sulfate, filtered, and concentrated in vacuo. Flash chromatography (Merck Silica gel 60, 230–400 mesh, 50/50 hexanes/ethyl acetate) afforded {N-{4-[2-cyclopentyl-1-(thiazol-2-ylcarbamoyl)-ethyl]-phenyl}-benzamide (95%) as a white solid: mp 285–290° C.; EI-HRMS m/e calcd for $C_{24}H_{25}N_3O_2S$ (M$^+$) 419.1667, found 419.1667.

EXAMPLE 2

3-Cyclopentyl-N-thiazol-2-yl-2-[4-(2-thiophen-2-yl-acetylamino)-phenyl]-propionamide

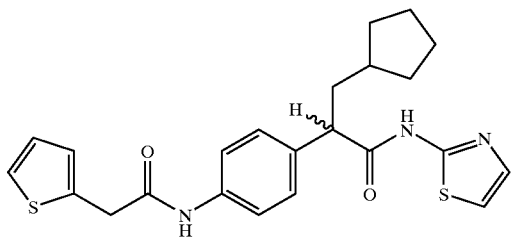

A solution of 2-(4-amino-phenyl)-3-cyclopentyl-propionic acid (prepared in Example 1, 49.0 mg, 0.21 mmol) in tetrahydrofuran (5 mL) at 25° C. was treated with N,N-diisopropylethylamine (0.04 mL, 0.25 mmol) and thiophen-2-yl-acetyl chloride (0.02 mL, 0.21 mmol). The reaction was stirred at 25° C. for 24 h. The reaction mixture was then concentrated in vacuo. Flash chromatography (Merck Silica gel 60, 230–400 mesh, 75/25 hexanes/ethyl acetate) afforded {N-{4-[2-cyclopentyl-1-(thiazol-2-ylcarbamoyl)-ethyl]-phenyl}-benzamide (61.0 mg, 81.2%) as a tan solid: mp 165–169° C.; EI-HRMS m/e calcd for $C_{20}H_{23}NO_3S$ ($M^+$) 357.1399, found 357.1398.

A solution of 3-cyclopentyl-2-[4-(2-thiophen-2-yl-acetylamino)-phenyl]-propionic acid (76.6 mg, 0.21 mmol), benzotriazol-1-yloxytris(dimethylamino)phosphonium hexafluorophosphate (142.0 mg, 0.32 mmol) and 2-aminothiazole (32.1 mg, 0.32 mmol) in methylene chloride (1 mL) at 25° C. was treated with triethylamine (0.9 mL, 0.64 mmol). The reaction mixture was stirred at 25° C. for 16 h. This mixture was then poured into water (50 mL) and extracted with methylene chloride (2×25 mL). The combined organic extracts were washed with a 1N aqueous sodium hydroxide solution (1×25 mL), a 1N aqueous hydrochloric acid solution (1×25 mL), water (1×25 mL), and a saturated aqueous sodium chloride solution (3×25 mL). The organic layer was dried over sodium sulfate, filtered, and concentrated in vacuo. Flash chromatography (Merck Silica gel 60, 230–400 mesh, 60/40 hexanes/ethyl acetate) afforded 3-cyclopentyl-N-thiazol-2-yl-2-[4-(2-thiophen-2-yl-acetylamino)-phenyl]-propionamide (82.7 mg, 87.8%) as a tan solid: mp 220–221° C.; EI-HRMS m/e calcd for $C_{23}H_{25}N_3O_2S_2$ ($M^+$) 4391388, found 439.1379.

EXAMPLE 3

3-Cyclopentyl-2-[4-(4-nitro-benzenesulfonylamino)-phenyl]-N-thiazol-2-yl-propionamide

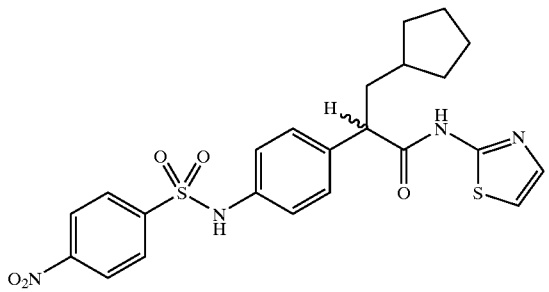

A solution of freshly prepared lithium diisopropylamide (430.55 mL of a 0.3M stock solution, 129.16 mmol) was cooled to −78° C. and then treated with a solution of (4-nitro-phenyl)-acetic acid ethyl ester (26.32 g, 125.83 mmol) in tetrahydrofuran/hexamethylphosphoramide (312.5 mL, 3:1). The resulting solution was stirred at −78° C. for 45 min. At this time, the reaction mixture was treated with a solution of iodomethylcyclopentane (27.75 g, 132.1 mmol) in hexamethylphosphoramide (27.75 mL). The mixture was stirred at −78° C. for 4 h. The reaction was then warmed to 25° C. and was stirred at 25° C. for 16 h. At this time, the reaction mixture was quenched by the dropwise addition of a saturated aqueous ammonium chloride solution (250 mL). This mixture was concentrated in vacuo, diluted with water (250 mL), and extracted with ethyl acetate (3×300 mL). The combined organic extracts were washed with a saturated aqueous lithium chloride solution (2×250 mL), dried over magnesium sulfate, filtered, and concentrated in vacuo. Flash chromatography (Merck Silica gel 60, 230–400 mesh, 98/2 hexanes/ethyl acetate) afforded 3-cyclopentyl-2-(4-nitro-phenyl)-propionic acid ethyl ester (28.30 g, 77.2%) as a yellow oil: EI-HRMS m/e calcd for $C_{16}H_{21}NO_4$ ($M^+$) 291.1470, found 291.1470.

A solution of 3-cyclopentyl-2-(4-nitro-phenyl)-propionic acid ethyl ester (14.1 g, 48.06 mmol) in tetrahydrofuran/water (300 mL, 3:1) was treated with lithium hydroxide (4.35 g, 103.67 mmol). The reaction was stirred at 25° C. for 21 h. The tetrahydrofuran was then removed in vacuo. The residue was diluted with water (75 mL) and extracted with diethyl ether (3×75 mL). The aqueous layer was acidified to pH=1 with a 3N aqueous hydrochloric acid solution and was extracted with methylene chloride (3×75 mL). The combined organic extracts were washed with a saturated aqueous sodium chloride solution (2×100 mL), dried over magnesium sulfate, filtered, and concentrated in vacuo to give 3-cyclopentyl-2-(4-nitro-phenyl)-propionic acid (11.97 g, 93.6%) as a yellow solid: mp 119–125° C.; EI-HRMS m/e calcd for $C_{14}H_{17}NO_4$ ($M^+$) 263.1157, found 263.1162.

A solution of 3-cyclopentyl-2-(4-nitro-phenyl)-propionic acid (131 mg, 0.5 mmol) in methylene chloride (5.0 mL) was cooled to 0° C. and then treated with a 2.0M solution of oxalyl chloride in methylene chloride (1 mL, 2.0 mmol) and a few drops of N,N-dimethylformamide. The reaction mixture was stirred at 0° C. for 15 min and at 25° C. for 30 min. The reaction mixture was then treated with a solution of 2-aminothiazole (110 mg, 1.0 mmol) in tetrahydrofuran (5 mL) and N,N-diisopropylethylamine (0.28 mL, 0.55 mmol). The solution was stirred at 25° C. for 24 h. At this time, the reaction was concentrated in vacuo. Flash chromatography (Merck Silica gel 60, 230–400 mesh, 50/50 hexanes/ethyl acetate) afforded 3-cyclopentyl-2-(4-nitro-phenyl)-N-thiazol-2-yl-propionamide (38 mg, 22.4%) as a yellow solid: mp 186–187° C.; EI-HRMS m/e calcd for $C_{17}H_{19}N_3O_3S$ ($M^+$) 345.1147, found 345.1148.

A solution of 3-cyclopentyl-2-(4-nitro-phenyl)-N-thiazol-2-yl-propionamide (345 mg, 1.0 mmol) in ethyl acetate (100 mL) was treated with 10% palladium on activated carbon (34.5 mg). The reaction mixture was stirred under 60 psi hydrogen gas at 25° C. for 6 h. The catalyst was then removed by filtration through a pad of celite and was washed with ethyl acetate. The filtrate was concentrated in vacuo to give 2-(4-amino-phenyl)-3-cyclopentyl-N-thiazol-2-yl-propionamide (288.3 mg, 91.4%) as a yellow solid: mp 102–107° C.; EI-HRMS m/e calcd for $C_{17}H_{21}N_3OS$ ($M^+$) 315.1405, found 315.1401.

A solution of 2-(4-amino-phenyl)-3-cyclopentyl-N-thiazol-2-yl-propionamide (63.0 mg, 0.20 mmol) in tetrahydrofuran (10 mL) was treated with N,N-diisopropylethylamine (0.04 mL, 0.24 mmol) and 4-nitrobenzene sulfonyl chloride (49.0 mg, 0.20 mmol). The reaction mixture was stirred at 25° C. for 21 h. At this time, the reaction was concentrated in vacuo. Flash chromatography (Merck Silica gel 60, 230–400 mesh, 50/50 hexanes/ethyl acetate) afforded 3-cyclopentyl-2-[4-(4-nitro-benzenesulfonylamino)-phenyl]-N-thiazol-2-yl-propionamide (47.5 mg, 47.5%) as a yellow solid: mp 120–125° C.; FAB-HRMS m/e calcd for $C_{23}H_{24}N_4O_5S_2$ $(M+H)^+$ 501.1266, found 501.1264.

EXAMPLE 4

N-{4-[2-Cyclopentyl-1-(thiazol-2-ylcarbamoyl)-ethyl]-phenyl}-isonicotinamide

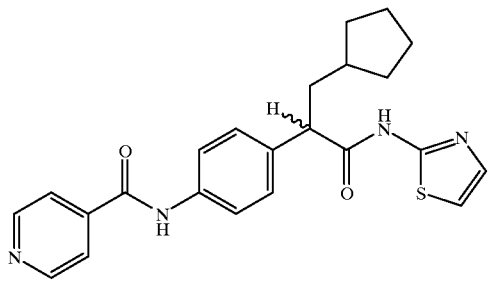

A solution of 2-(4-amino-phenyl)-3-cyclopentyl-N-thiazol-2-yl-propionamide (prepared in Example 3, 63.0 mg, 0.20 mmol) in tetrahydrofuran (10 mL) was treated with N,N-diisopropylethylamine (0.082 mL, 0.47 mmol) and isonicotinoyl chloride (35.6 mg, 0.20 mmol). The reaction mixture was stirred at 25° C. for 24 h. At this time, the reaction was concentrated in vacuo. Flash chromatography (Merck Silica gel 60, 230–400 mesh, 90/10 ethyl acetate/methanol) afforded N-{4-[2-cyclopentyl-1-(thiazol-2-ylcarbamoyl)-ethyl]-phenyl}-isonicotinamide (65.5 mg, 77.9%) as a white solid: mp 225–230° C.; FAB-HRMS m/e calcd for $C_{23}H_{24}N_4O_2S$ $(M+H)^+$ 421.1698, found 421.1698.

EXAMPLE 5

N-{4-[2-Cyclopentyl-1-(thiazol-2-ylcarbamoyl)-ethyl]-phenyl}-4-nitro-benzamide

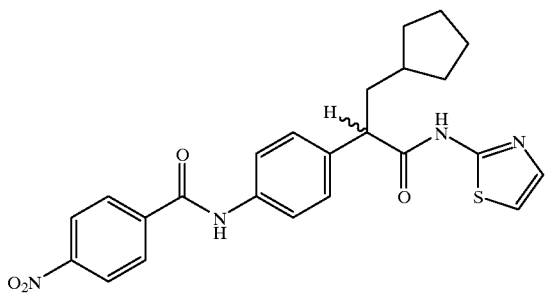

A solution of 2-(4-amino-phenyl)-3-cyclopentyl-N-thiazol-2-yl-propionamide (prepared in Example 3, 63.0 mg, 0.20 mmol) in tetrahydrofuran (10 mL) was treated with N,N-diisopropylethylamine (0.04 mL, 0.24 mmol) and 4-nitro-benzoyl chloride (49.0 mg, 0.26 mmol). The reaction mixture was stirred at 25° C. for 21 h. At this time, the reaction was concentrated in vacuo. The residue was triturated with diethyl ether to afford N-{4-[2-cyclopentyl-1-(thiazol-2-ylcarbamoyl)-ethyl]-phenyl}-4-nitro-benzamide (73.7 mg, 79.3%) as a pale yellow solid: mp 236–238° C.; FAB-HRMS m/e calcd for $C_{24}H_{24}N_4O_4S$ $(M+H)^+$ 465.1596, found 465.1617.

EXAMPLE 6

N-{4-[2-Cyclopentyl-1-(thiazol-2-ylcarbamoyl)-ethyl]-phenyl}-oxalamic acid methyl ester

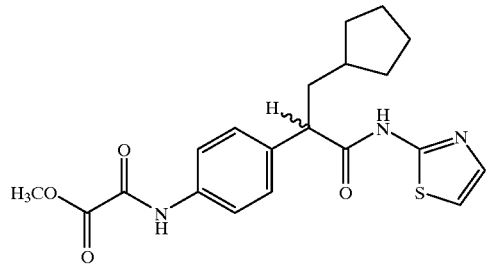

A solution of 2-(4-amino-phenyl)-3-cyclopentyl-N-thiazol-2-yl-propionamide (prepared in Example 3, 78 mg, 0.25 mmol) in tetrahydrofuran (10 mL) was treated with N,N-diisopropylethylamine (0.05 mL, 0.30 mmol) and methyl oxalyl chloride (0.02 mL, 0.25 mmol). The reaction mixture was stirred at 25° C. for 16 h. At this time, the reaction was concentrated in vacuo. High pressure liquid chromatography (Chromegasphere SI-60, 10 µM, 60 Å, 25 cm×23 cm ID, 70/30 heptane/ethyl acetate) afforded N-{4-[2-cyclopentyl-1-(thiazol-2-ylcarbamoyl)-ethyl]-phenyl}-oxalamic acid methyl ester (13.7 mg, 13.6%) as a white solid: mp 95–98° C.; EI-HRMS m/e calcd for $C_{20}H_{23}N_3O_4S$ $(M^+)$ 401.1409, found 401.1402.

EXAMPLE 7

Acetic acid {4-[2-cyclopentyl-1-(thiazol-2-ylcarbamoyl)-ethyl]-phenylcarbamoyl}-methyl ester

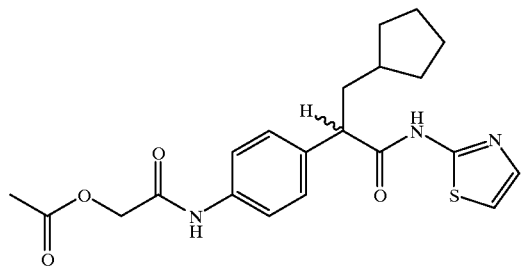

A solution of 2-(4-amino-phenyl)-3-cyclopentyl-N-thiazol-2-yl-propionamide (prepared in Example 3, 105 mg, 0.33 mmol) in tetrahydrofuran (10 mL) was treated with N,N-diisopropylethylamine (0.068 mL, 0.40 mmol) and acetoxy acetyl chloride (0.03 mL, 0.33 mmol). The reaction mixture was stirred at 25° C. for 5 h. At this time, the reaction was concentrated in vacuo. High pressure liquid chromatography (Chromegasphere SI-60, 10 µM, 60 Å, 25 cm×23 cm ID, 50/50 heptane/ethyl acetate) afforded acetic acid {4-[2-cyclopentyl-1-(thiazol-2-ylcarbamoyl)-ethyl]-phenylcarbamoyl}-methyl ester (31.4 mg, 22.7%) as a white solid: mp 90–95° C.; EI-HRMS m/e calcd for $C_{21}H_{25}N_3O_4S$ $(M^+)$ 415.1565, found 415.1567.

EXAMPLE 8

N-{4-[2-Cyclopentyl-1-(thiazol-2-ylcarbamoyl)-ethyl]-phenyl}-dimethylsulfamide

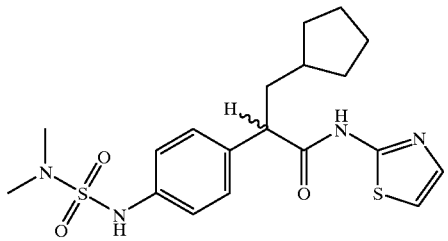

A solution of 2-(4-amino-phenyl)-3-cyclopentyl-N-thiazol-2-yl-propionamide (prepared in Example 3, 105 mg, 0.33 mmol) in pyridine (5 mL) was treated with dimethyl-sulfamoyl chloride (0.04 mL, 0.38 mmol). The reaction mixture was stirred at 25° C. for 24 h. At this time, the reaction was concentrated in vacuo. The residue was dissolved in methylene chloride, and the organic phase was washed with a 1N aqueous hydrochloric acid solution, a saturated aqueous sodium bicarbonate solution, and a saturated aqueous sodium chloride solution. The organic layer was dried over magnesium sulfate, filtered, and concentrated in vacuo. High pressure liquid chromatography (Chromegasphere SI-60, 10 μM, 60 Å, 25 cm×23 cm ID, 60/40 heptane/ethyl acetate) afforded the N-{4-[2-cyclopentyl-1-(thiazol-2-ylcarbamoyl)-ethyl]-phenyl}-dimethylsulfamide (21.3%) as a white solid: mp 110–112° C.; FAB-HRMS m/e calcd for $C_{19}H_{26}N_4O_3S_2$ (M+H)$^+$ 423.1524, found 423.1524.

EXAMPLE 9

N-{4-[2-Cyclopentyl-1-(thiazol-2-ylcarbamoyl)-ethyl]-phenyl}-nicotinamide

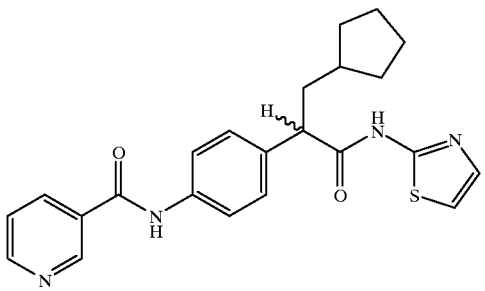

A solution of 2-(4-amino-phenyl)-3-cyclopentyl-N-thiazol-2-yl-propionamide (prepared in Example 3, 63.0 mg, 0.20 mmol) in tetrahydrofuran (10 mL) was treated with N,N-diisopropylethylamine (0.082 mL, 0.48 mmol) and nicotinoyl chloride hydrochloride (35.6 mg, 0.20 mmol). The reaction mixture was stirred at 25° C. for 24 h. At this time, the reaction was concentrated in vacuo. Flash chromatography (Merck Silica gel 60, 230–400 mesh, 90/10 ethyl acetate/methanol) afforded N-{4-[2-cyclopentyl-1-(thiazol-2-ylcarbamoyl)-ethyl]-phenyl}-nicotinamide (58.9 mg, 70%) as a white solid: mp 240–242° C.; EI-HRMS m/e calcd for $C_{23}H_{24}N_4O_2S$ (M$^+$) 420.1619, found 420.1625.

EXAMPLE 10

2-(3-Cyclopentyl-2-{4-[(pyridine-3-carbonyl)-amino]-phenyl}propionylamino)-thiazole-4-carboxylic acid ethyl ester

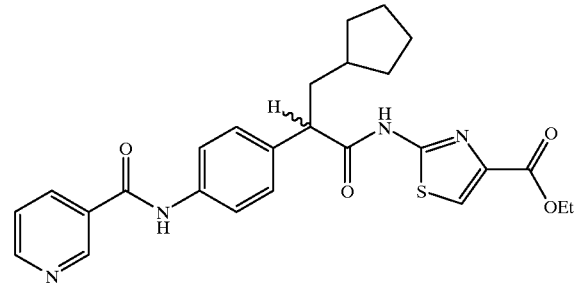

A solution of freshly prepared lithium diisopropylamide (430.55 mL of a 0.3M stock solution, 129.16 mmol) was cooled to −78° C. and then treated with a solution of (4-nitro-phenyl)-acetic acid ethyl ester (26.32 g, 125.83 mmol) in tetrahydrofuran/hexamethylphosphoramide (312.5 mL, 3:1). The resulting solution was stirred at −78° C. for 45 min. At this time, the reaction was treated with a solution of iodomethylcyclopentane (27.75 g, 132.1 mmol) in hexamethylphosphoramide (27.75 mL). The mixture was stirred at −78° C. for 4 h. The reaction was then warmed to 25° C. and was stirred at 25° C. for 16 h. At this time, the reaction mixture was quenched by the dropwise addition of a saturated aqueous ammonium chloride solution (250 mL). This mixture was concentrated in vacuo, diluted with water (250 mL), and extracted with ethyl acetate (3×300 mL). The combined organic extracts were washed with a saturated aqueous lithium chloride solution (2×250 mL), dried over magnesium sulfate, filtered, and concentrated in vacuo. Flash chromatography (Merck Silica gel 60, 230–400 mesh, 98/2 hexanes/ethyl acetate) afforded 3-cyclopentyl-2-(4-nitro-phenyl)-propionic acid ethyl ester (28.30 g, 77.2%) as an yellow oil: EI-HRMS m/e calcd for $C_{16}H_{21}NO_4$ (M$^+$) 291.1470, found 291.1470.

A solution of 3-cyclopentyl-2-(4-nitro-phenyl)-propionic acid ethyl ester (14.1 g, 48.06 mmol) in tetrahydrofuran/water (300 mL, 3:1) was treated with lithium hydroxide (4.35 g, 103.67 mmol). The reaction was stirred at 25° C. for 21 h. The tetrahydrofuran was then removed in vacuo. The residue was diluted with water (75 mL) and extracted with ether (3×75 mL). The aqueous layer was acidified to pH=1 with a 3N aqueous hydrochloric acid solution and was extracted with methylene chloride (3×75 mL). The combined organic extracts were washed with a saturated aqueous sodium chloride solution (2×100 mL), dried over magnesium sulfate, filtered, and concentrated in vacuo to afford 3-cyclopentyl-2-(4-nitro-phenyl)-propionic acid (11.97 g, 93.6%) as a yellow solid: mp 119–125° C.; EI-HRMS m/e calcd for $C_{14}H_{17}NO_4$ (M$^+$) 263.1157, found 263.1162.

A solution of 3-cyclopentyl-2-(4-nitro-phenyl)-propionic acid (100 mg, 0.38 mmol) in ethyl acetate (50 mL) was treated with 10% palladium on activated carbon. The reaction mixture was stirred under 60 psi of hydrogen gas at 25° C. for 16 h. The catalyst was removed by filtration through a pad of celite and was washed with ethyl acetate. The filtrate was concentrated in vacuo to afford 2-(4-amino-phenyl)-3-cyclopentyl-propionic acid (120 mg, 100%) as a white solid: mp 167–169° C.; EI-HRMS m/e calcd for $C_{14}H_{19}NO_2$ (M$^+$) 233.1415, found 233.1413.

17

A solution of 2-(4-amino-phenyl)-3-cyclopentyl-propionic acid (130 mg, 0.56 mmol) in tetrahydrofuran (10 mL) at 25° C. was treated with N,N-diisopropylethylamine (0.23 mL, 1.34 mmol) and nicotinoyl chloride hydrochloride (99 mg, 0.54 mmol). The reaction mixture was stirred at 25° C. for 48 h. At this time, the reaction was concentrated in vacuo. High pressure liquid chromatography (Chromegasphere SI-60, 10 μM, 60 Å, 25 cm×23 cm ID, 90/10 ethyl acetate/heptane) afforded 3-cyclopentyl-2-{4-[(pyridine-3-carbonyl)-amino]-phenyl}-propionic acid (40.9 mg, 21.7%) as a yellow solid: mp 160–163° C.; EI-HRMS m/e calcd for $C_{21}H_{23}NO_3$ ($M^+$) 337.1677, found 337.1670.

A solution of 3-cyclopentyl-2-{4-[(pyridine-3-carbonyl)-amino]-phenyl}-propionic acid (233 mg, 0.66 mmol) in methylene chloride (10 mL) was cooled to 0° C. and then treated with a 2.0M solution of oxalyl chloride in methylene chloride (0.36 mL, 0.72 mmol) and a few drops of N,N-dimethylformamide. The reaction mixture was stirred at 0° C. for 15 min and at 25° C. for 30 min. The reaction mixture was then treated with a solution of 2-amino-thiazole-4-carboxylic acid ethyl ester (367 mg, 1.45 mmol) in tetrahydrofuran (5 mL) and N,N-diisopropylethylamine (0.40 mL, 2.31 mmol). This solution was stirred at 25° C. for 48 h. At this time, the reaction was concentrated in vacuo. High pressure liquid chromatography (Chromegasphere SI-60, 10 μM, 60 Å, 25 cm×23 cm ID, 95/5 ethyl acetate/heptane) afforded 2-(3-cyclopentyl-2-{4-[(pyridine-3-carbonyl)-amino]-phenyl}propionylamino)-thiazole-4-carboxylic acid ethyl ester (40.5 mg, 12.5%) as an off-white: mp 222–223° C.; EI-HRMS m/e calcd for $C_{26}H_{28}N_4O_4S$ ($M^+$) 492.1831, found 492.1835.

EXAMPLE 11

[2-(3-Cyclopentyl-2-{4-[(pyridine-3-carbonyl)-amino]-phenyl}-propionylamino)-thiazol-4-yl]-acetic acid ethyl ester

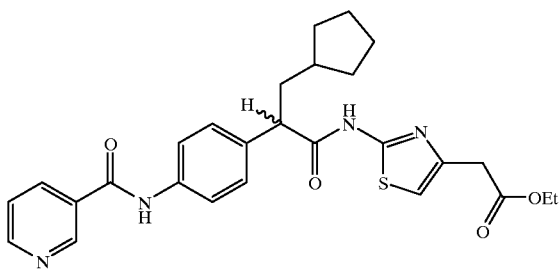

A solution of 3-cyclopentyl-2-(4-[(pyridine-3-carbonyl)-amino]-phenyl}-propionic acid (prepared in Example 10, 169 mg, 0.50 mmol) in methylene chloride (10 mL) at 25° C. was treated with triethylamine (0.21 mL, 1.3 mmol), benzotriazol-1-yloxytris(dimethylamino)phosphonium hexafluorophosphate (332 mg, 0.75 mmol), and (2-amino-thiazol-4-yl)-acetic acid ethyl ester (140 mg, 0.75 mmol). The reaction mixture was stirred at 25° C. for 20 h. At this time, the reaction was diluted with methylene chloride (50 mL). This solution was washed with a 1N aqueous hydrochloric acid solution (1×15 mL), water (1×15 mL), and a saturated aqueous sodium chloride solution (2×25 mL). The organic layer was dried over magnesium sulfate, filtered, and concentrated in vacuo. Flash chromatography (Merck Silica gel 60, 230–400 mesh, 100% ethyl acetate) afforded [2-(3-cyclopentyl-2-{4-[(pyridine-3-carbonyl)-amino]-

18 phenyl}-propionylamino)-thiazol-4-yl]-acetic acid ethyl ester (100.1 mg, 39.5%) as white solid: mp 195–200° C.; EI-HRMS m/e calcd for $C_{27}H_{30}N_4O_4S$ ($M^+$) 506.1987, found 506.1985.

EXAMPLE 12

3-Cyclopentyl-2-(4-methanesulfonylamino-phenyl)-N-thiazol-2-yl-propionamide

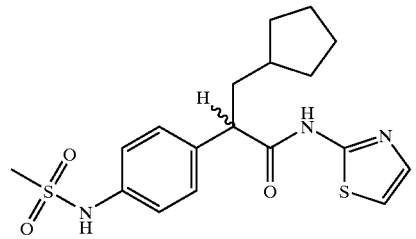

A solution of 2-(4-amino-phenyl)-3-cyclopentyl-N-thiazol-2-yl-propionamide (prepared in Example 3, 158 mg, 0.5 mmol) in pyridine (5 mL) at 25° C. was treated with methanesulfonyl chloride (50 μL, 0.57 mmol). The reaction was stirred at 25° C. for 7 h and was then concentrated in vacuo. High pressure liquid chromatography (Chromegasphere SI-60, 10 μM, 60 Å, 25 cm×23 cm ID, 40/60 heptane/ethyl acetate) afforded 3-cyclopentyl-2-(4-methanesulfonylamino-phenyl)-N-thiazol-2-yl-propionamide (98.2 mg, 49.9%) as a tan solid: mp 85–90° C.; EI-HRMS m/e calcd for $C_{18}H_{23}N_3O_3S$ ($M^+$) 393.1180, found 393.1185.

EXAMPLE 13

3-Cyclopentyl-N-thiazol-2-yl-2-(4-trifluoromethanesulfonylamino-phenyl)-propionamide

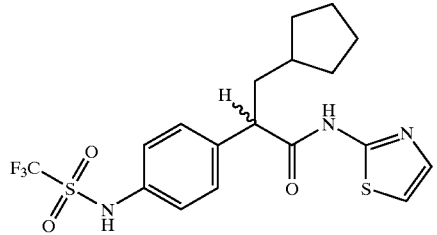

A solution of 2-(4-amino-phenyl)-3-cyclopentyl-N-thiazol-2-yl-propionamide (prepared in Example 3, 158 mg, 0.5 mmol) in pyridine (5 mL) at 25° C. was treated with trifluoromethanesulfonyl chloride (60 μL, 0.57 mmol). The reaction was stirred at 25° C. for 7 h and was then concentrated in vacuo. High pressure liquid chromatography (Chromegasphere SI-60, 10 μM, 60 Å, 25 cm×23 cm ID, 40/60 heptane/ethyl acetate) afforded the 3-cyclopentyl-N-thiazol-2-yl-2-(4-trifluoromethanesulfonylamino-phenyl)-propionamide (93.8 mg, 41.9%) as a tan solid: mp 70–74° C.; EI-HRMS m/e calcd for $C_{18}H_{20}F_3N_3O_3S_2$ ($M^+$) 447.0898, found 447.0894.

EXAMPLE 14

3-Cyclopentyl-N-thiazol-2-yl-2-[4-(2,2,2-trifluoro-ethanesulfonylamino)-phenyl]-propionamide

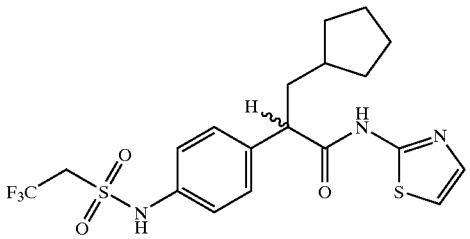

A solution of 2-(4-amino-phenyl)-3-cyclopentyl-N-thiazol-2-yl-propionamide (prepared in Example 3, 158 mg, 0.5 mmol) in pyridine (5 mL) at 25° C. was treated with 2,2,2-trifluoroethanesulfonyl chloride (63.5 μL, 0.57 mmol). The reaction was stirred at 25° C. for 48 h and was then concentrated in vacuo. High pressure liquid chromatography (Chromegasphere SI-60, 10 μM, 60 Å, 25 cm×23 cm ID, 40/60 heptane/ethyl acetate) afforded the 3-cyclopentyl-N-thiazol-2-yl-2-[4-(2,2,2-trifluoro-ethanesulfonylamino)-phenyl]-propionamide (98.1 mg, 42.4%) as a light yellow oil: EI-HRMS m/e calcd for $C_{19}H_{22}F_3N_3O_3S_2$ (M$^+$) 461.1054, found 461.1064.

EXAMPLE 15

N-{4-[2-Cyclopentyl-1-(pyridin-2-ylcarbamoyl)-ethyl]-phenyl}-nicotinamide

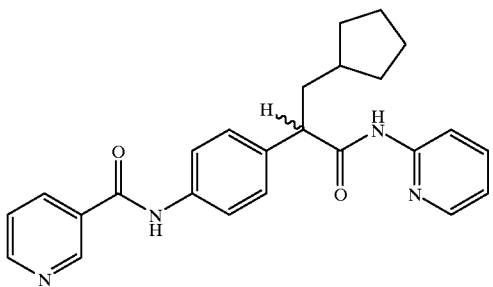

A solution of 3-cyclopentyl-2-(4-nitro-phenyl)-propionic acid (prepared in Example 1, 263 mg, 1.0 mmol) in methylene chloride (5 mL) was cooled to 0° C. and then treated with a 2.0M solution of oxalyl chloride in methylene chloride (0.60 mL, 1.2 mmol) and a few drops of N,N-dimethylformamide. The reaction mixture was stirred at 0° C. for 15 min and at 25° C. for 1 h. The reaction was then treated with a solution of 2-aminopyridine (207 mg, 2.2 mmol) in tetrahydrofuran (5 mL) and N,N-diisopropylethylamine (0.42 mL, 2.5 mmol). This solution was stirred at 25° C. for 24 h. At this time, the reaction was concentrated in vacuo. Flash chromatography (Merck Silica gel 60, 230–400 mesh, 80/20 hexanes/ethyl acetate) afforded 3-cyclopentyl-2-(4-nitro-phenyl)-N-pyridin-2-yl-propionamide (110.2 mg, 32.5%) as a white solid: mp 152–154° C.; EI-HRMS m/e calcd for $C_{19}H_{21}N_3O_3$ (M$^+$) 339.1582, found 339.1581.

A solution of 3-cyclopentyl-2-(4-nitro-phenyl)-N-pyridin-2-yl-propionamide (130 mg, 0.38 mmol) in ethyl acetate (50 mL) and methanol (5 mL) was treated with 10% palladium on activated carbon (50 mg). The reaction mixture was shaken under 60 psi of hydrogen gas at 25° C. for 18 h. The catalyst was then removed by filtration through a pad of celite and washed with ethyl acetate. The filtrate was concentrated in vacuo to afford 2-(4-amino-phenyl)-3-cyclopentyl-N-pyridin-2-yl-propionamide (99.9 mg, 84.3%) as a tan oil: EI-HRMS m/e calcd for $C_{21}H_{23}N_3O$ (M$^+$) 309.1841, found 309.1849.

A solution of 2-(4-amino-phenyl)-3-cyclopentyl-N-pyridin-2-yl-propionamide (81.7 mg, 0.26 mmol) in tetrahydrofuran (10 mL) at 25° C. was treated with N,N-diisopropylethylamine (0.11 mL, 0.63 mmol) and nicotinoyl chloride hydrochloride (47 mg, 0.26 mmol). The resulting reaction mixture was stirred at 25° C. for 48 h. At this time, the reaction was concentrated in vacuo. High pressure liquid chromatography (Chromegasphere SI-60, 10 μM, 60 Å, 25 cm×23 cm ID, 90/10 ethyl acetate/heptane) afforded N-{4-[2-cyclopentyl-1-(pyridin-2-ylcarbamoyl)-ethyl]-phenyl}-nicotinamide (40.9 mg, 21.7%) as a yellow solid: mp 160–163° C.; EI-HRMS m/e calcd for $C_{25}H_{26}N_4O_2$ (M$^+$) 414.2055, found 414.2056.

EXAMPLE 16

6-(3-Cyclopentyl-2-{4-[(pyridine-3-carbonyl)-amino]-phenyl}-propionylamino)-nicotinic acid methyl ester

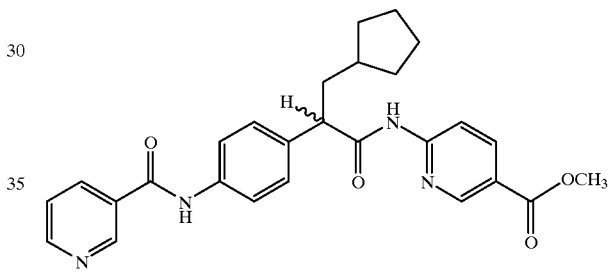

A solution of 3-cyclopentyl-2-(4-nitro-phenyl)-propionic acid (prepared in Example 1, 526 mg, 2.0 mmol) in methylene chloride (20 mL) was cooled to 0° C. and then treated with a 2.0M solution of oxalyl chloride in methylene chloride (1.2 mL, 2.4 mmol) and a few drops of N,N-dimethylformamide. The reaction mixture was stirred at 0° C. for 10 min and at 25° C. for 30 min. The reaction mixture was then treated with a solution of 6-amino-nicotinic acid methyl ester (532 mg, 3.5 mmol) and N,N-diisopropylethylamine (0.84 mL, 4.82 mmol) in tetrahydrofuran (10 mL). The reaction mixture was stirred at 25° C. for 48 h. At this time, the reaction was concentrated in vacuo. High pressure liquid chromatography (Chromegasphere SI-60, 10 μM, 60 Å, 25 cm×23 cm ID, 50/50 heptane/ethyl acetate) afforded 6-[3-cyclopentyl-2-(4-nitro-phenyl)-propionylamino]-nicotinic acid methyl ester (353.9 mg, 44.6%) as a pale orange oil: EI-HRMS m/e calcd for $C_{21}H_{23}N_3O_5$ (M$^+$) 397.1637, found 397.1631.

A solution of 6-[3-cyclopentyl-2-(4-nitro-phenyl)-propionylamino]-nicotinic acid methyl ester (300 mg, 0.75 mmol) in ethyl acetate (30 mL) and methanol (5 mL) was treated with 10% palladium on activated carbon (30 mg). The reaction mixture was shaken under 60 psi of hydrogen gas at 25° C. for 16 h. The catalyst was then removed by filtration through a pad of celite and washed with ethyl acetate. The filtrate was concentrated in vacuo to afford 6-[2-(4-amino-phenyl)-3-cyclopentyl-propionylamino]- nicotinic acid methyl ester (277.4 mg, quant) as a pale yellow glass: mp 65–68° C.; EI-HRMS m/e calcd for $C_{21}H_{25}N_3O_3$ ($M^+$) 367.1893, found 367.1899.

A solution of 6-[2-(4-amino-phenyl)-3-cyclopentyl-propionylamino]-nicotinic acid methyl ester (236.1 mg, 0.65 mmol) in tetrahydrofuran (15 mL) at 25° C. was treated with N,N-diisopropylethylamine (0.27 mL, 1.54 mmol) and nicotinoyl chloride hydrochloride (115 mg, 0.64 mmol). The reaction mixture was stirred at 25° C. for 48 h. At this time, the reaction was concentrated in vacuo. Flash chromatography (Merck Silica gel 60, 230–400 mesh, 90/10 ethyl acetate/hexanes) afforded 6-(3-cyclopentyl-2-{4-[(pyridine-3-carbonyl)-amino]phenyl}-propionylamino)-nicotinic acid methyl ester (219.6 mg, 72.3%) as a white solid: mp 110–115° C.; EI-HRMS m/e calcd for $C_{27}H_{28}N_4O_4$ ($M^+$) 472.2110, found 472.2109.

EXAMPLE 17

6-(3-Cyclopentyl-2-(4-[(pyridine-3-carbonyl)-amino]-phenyl}-propionylamino)-nicotinic acid

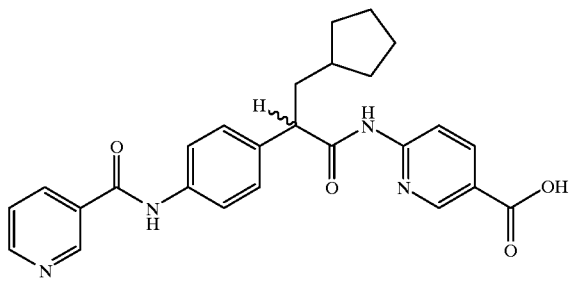

A solution of 6-(3-cyclopentyl-2-{4-[(pyridine-3-carbonyl)-amino]-phenyl}-propionylamino)-nicotinic acid methyl ester (prepared in Example 16, 87.2 mg, 0.18 mmol) in tetrahydrofuran (8 mL) and water (2 mL) was treated with lithium hydroxide (17.0 mg, 0.41 mmol). The reaction was stirred at 25° C. for 20 h. At this time, the reaction was concentrated in vacuo. The residue was diluted with water (25 mL) and extracted with diethyl ether (1×20 mL). The aqueous layer was acidified to pH=1 with a 3N aqueous hydrochloric acid solution and was extracted with methylene chloride (3×50 mL). The combined organic extracts were washed with water (1×50 mL) and a saturated aqueous sodium chloride solution (2×50 mL), dried over magnesium sulfate, filtered, and concentrated in vacuo. High pressure liquid chromatography (Chromegasphere SI-60, 10 µM, 60 Å, 25 cm×23 cm ID, 100% ethyl acetate with acetic acid) afforded 6-[3-cyclopentyl-2-(4-nitro-phenyl)-propionylamino]-nicotinic acid (6.4 mg, 7.5%) as a pale yellow oil: EI-HRMS m/e calcd for $C_{16}H_{26}N_4O_4$ ($M^+$) 458.1954, found 458.1967.

Biological Activity Examples

Example A

In Vitro Glucokinase Activity

Glucokinase Assay: Glucokinase (GK) was assayed by coupling the production of glucose-6-phosphate to the generation of NADH with glucose-6-phosphate dehydrogenase (G6PDH, 0.75-1 kunits/mg; Boehringer Mannheim, Indianapolis, Ind.) from *Leuconostoc mesenteroides* as the coupling enzyme (Scheme 2). Recombinant Scheme 2

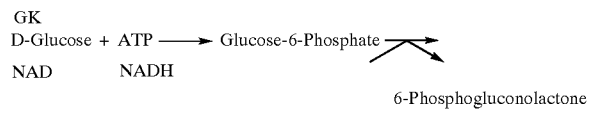

Human liver GK1 was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C. in a flat bottom 96-well tissue culture plate from Costar (Cambridge, Mass.) with a final incubation volume of 120 µl. The incubation mixture contained: 25 mM Hepes buffer (pH, 7.1), 25 mM KCl, 5 mM D-glucose, 1 mM ATP, 1.8 mM NAD, 2 mM $MgCl_2$, 1 µM sorbitol-6-phosphate, 1 mM dithiothreitol, test drug or 10% DMSO, 1.8 unit/ml G6PDH, and GK (see below). All organic reagents were >98% pure and were from Boehringer Mannheim with the exceptions of D-glucose and Hepes that were from Sigma Chemical Co, St Louis, Mo. Test compounds were dissolved in DMSO and were added to the incubation mixture minus GST-GK in a volume of 12 µl to yield a final DMSO concentration of 10%. This mix was preincubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 µl GST-GK.

After addition of enzyme, the increase in optical density (OD) at 340 nm was monitored over a 10 minute incubation period as a measure of GK activity. Sufficient GST-GK was added to produce an increase in $OD_{340}$ of 0.08 to 0.1 units over the 10 minute incubation period in wells containing 10% DMSO, but no test compound. Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of GK, i.e., the $SC_{1.5}$, was calculated. All of the compounds of formula I described in the Synthesis Examples had an $SC_{1.5}$ less than or equal to 30 µM.

What is claimed is:
1. An amide of formula

I-B

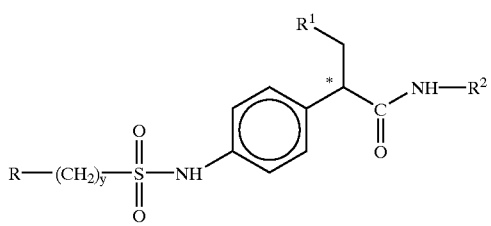

wherein R is

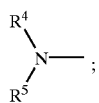

$R^1$ is cycloalkyl;
$R^2$ is an unsubstituted or substituted thiazole;
$R^4$ and $R^5$ are independently hydrogen or lower alkyl; and y is an integer from 1–5, or a pharmaceutically acceptable salt thereof.

2. The compound of claim 1 wherein $R^1$ is cyclopentyl.

3. The amide of claim 1 wherein said compound is N-{4-[2-cyclopentyl-1-(thiazol-2-ylcarbamoyl)-ethyl]-phenyl}-dimethylsulfamide.

* * * * *

UNITED STATES PATENT AND TRADEMARK OFFICE
CERTIFICATE OF CORRECTION

PATENT NO. : 6,489,485 B2
DATED : December 3, 2002
INVENTOR(S) : Fred T. Bizzaro et al.

It is certified that error appears in the above-identified patent and that said Letters Patent is hereby corrected as shown below:

<u>Title page,</u>
Item [75], delete the address of the third named co-inventor, and insert therefor -- Pine Brook, NJ (US) --.

Signed and Sealed this

Sixth Day of May, 2003

JAMES E. ROGAN
*Director of the United States Patent and Trademark Office*